United States Patent [19]

Galpin et al.

[11] Patent Number: 5,505,705
[45] Date of Patent: Apr. 9, 1996

[54] NEEDLE HOUSINGS

[75] Inventors: Kim R. Galpin, Merewether; Graeme F. Walton, Valentine, both of Australia

[73] Assignee: Needle Technology (AUST) Limited, New South Wales, Australia

[21] Appl. No.: 104,080

[22] PCT Filed: Feb. 3, 1992

[86] PCT No.: PCT/AU92/00035

§ 371 Date: Nov. 12, 1993

§ 102(e) Date: Nov. 12, 1993

[87] PCT Pub. No.: WO92/13585

PCT Pub. Date: Aug. 20, 1992

[30] Foreign Application Priority Data

Feb. 11, 1991 [AU] Australia ................. PK4555
Aug. 15, 1991 [AU] Australia ................. PK7789

[51] Int. Cl.[6] .................................... A61M 5/00
[52] U.S. Cl. ................ 604/192; 604/263; 128/919
[58] Field of Search .................... 604/192, 263, 604/187, 110, 111; 128/919

[56] References Cited

U.S. PATENT DOCUMENTS

| | | | |
|---|---|---|---|
| 4,488,643 | 12/1984 | Pepper. | |
| 4,559,042 | 12/1985 | Voteh | 604/192 |
| 4,610,667 | 9/1986 | Pedicano | 604/192 |
| 4,623,336 | 11/1986 | Pedicano | 604/192 |
| 4,659,330 | 4/1987 | Nelson | 604/192 |
| 4,717,386 | 6/1988 | Simmons | 604/192 |
| 4,735,617 | 4/1988 | Nelson | 604/192 |
| 4,840,618 | 6/1989 | Marvel | 604/187 |
| 4,876,488 | 10/1989 | Gentile | 315/378 |
| 4,892,525 | 1/1990 | Hermann | 604/263 |
| 4,973,315 | 11/1990 | Sincock | 604/192 |
| 4,986,817 | 1/1991 | Code | 604/192 |
| 4,994,044 | 2/1991 | LoDuca | 604/192 |
| 5,078,696 | 1/1992 | Nedbaluk | 604/192 |

FOREIGN PATENT DOCUMENTS

| | | |
|---|---|---|
| 3783385 | 7/1985 | Australia. |
| 5371286 | 8/1986 | Australia. |
| 7712987 | 2/1988 | Australia. |
| 1120288 | 8/1988 | Australia. |
| 3440589 | 11/1989 | Australia. |
| 3840289 | 2/1990 | Australia. |
| 2669988 | 6/1990 | Australia. |
| 4559089 | 8/1990 | Australia. |
| 8140687 | 9/1990 | Australia. |
| 7153391 | 7/1991 | Australia. |
| 2446188 | 9/1991 | Australia. |
| 4328689 | 2/1993 | Australia. |
| 364839 | 4/1990 | European Pat. Off.. |
| 1195865 | 8/1989 | Japan. |
| 249666 | 2/1990 | Japan. |
| 2209470 | 5/1989 | United Kingdom. |
| 2220354 | 1/1990 | United Kingdom. |
| 2222370 | 3/1990 | United Kingdom. |
| 8808313 | 11/1988 | WIPO. |

OTHER PUBLICATIONS

Patent Abstracts of Japan, C651 p. 6, JP–A–1–195865 (Eisuke Imanaga) 7 Aug. 1989.
Patent Abstracts of Japan, C716, p. 78, JP,A,2–49666) (Terumo Corp) 20 Feb. 1990.

*Primary Examiner*—John D. Yasko
*Attorney, Agent, or Firm*—Ladas & Parry

[57] ABSTRACT

A needle housing (1) comprises a conical wall portion (2) and a cylindrical wall portion (3) with annular skirt (4) and annular base (5). Base (5) has located beneath it a layer of an adhesive impregnated material (6) or alternatively a roughened anti-slip friction surface. An internal annular rib (7) extends inwardly from skirt (4). Annular rib (7) is adapted to frictionally engage surface (16) of the external peripheral surface of needle boss (12) prior to use. Located above rib (7) is an O-ring (13). O-ring (13) is discarded upon removal of needle boss (12) from housing (1). Housing (1) is attached or otherwise supported above a fixed horizontal surface prior to removal of needle (10) and needle boss (12) for use. After use the boss (12) and needle (10) are reinserted into housing (1) so as to be safely retained therein beneath rib (7).

11 Claims, 2 Drawing Sheets

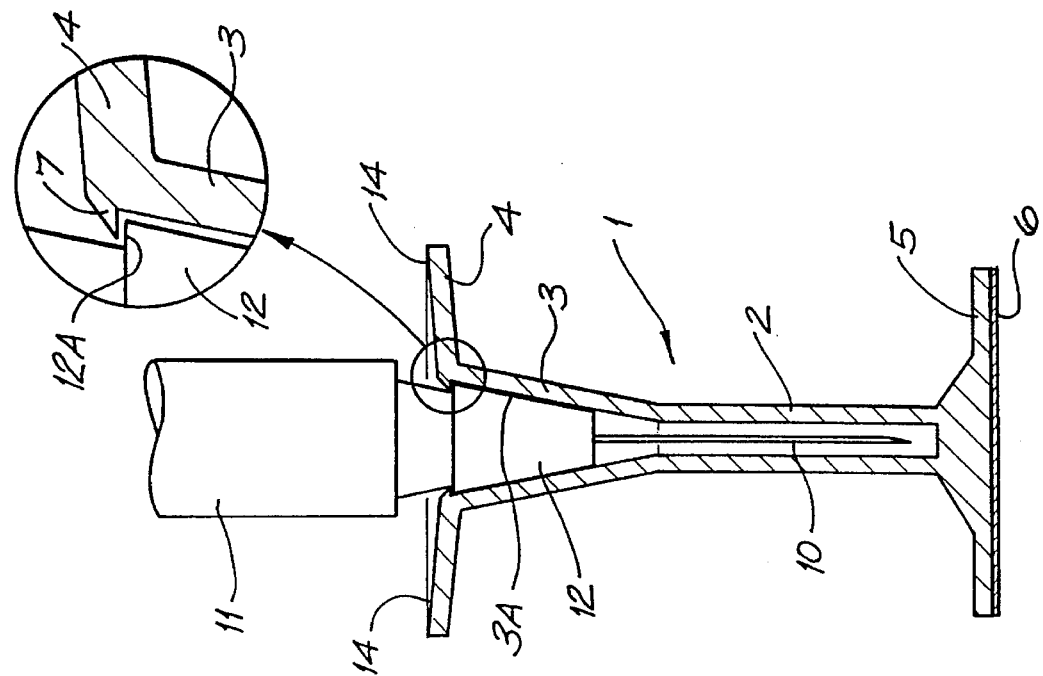
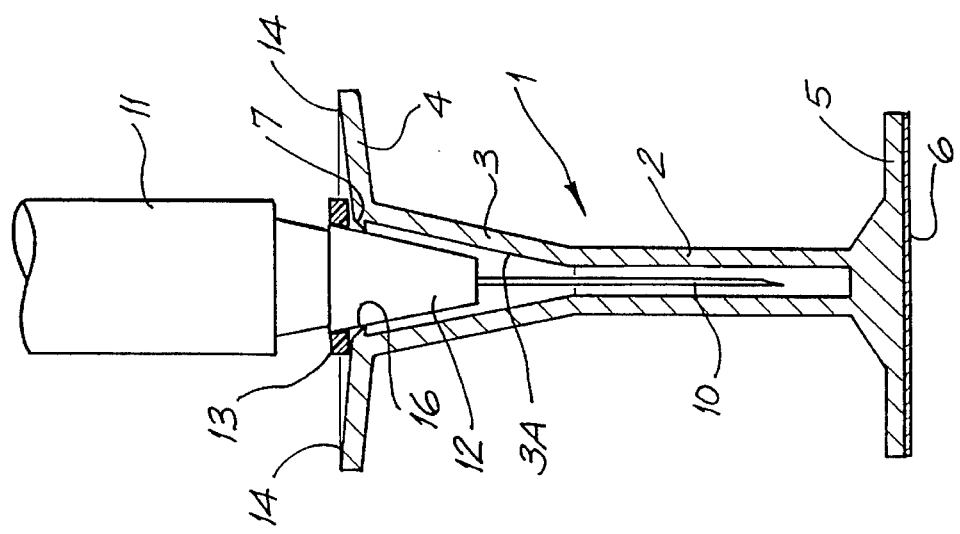

NEEDLE HOUSINGS

FIELD OF THE INVENTION

This invention relates to needle housings and more particularly to such housings as might accommodate a needle used in the medical profession or in personal drug administration so that the physician, surgeon or other needle operator might be protected from injury by the needle after its use.

The danger of injury and possible infection with the HIV or hepatitis B virus to medical practitioners using needles in the normal course of their business is well documented. Further, persons who are in the habit of administering drugs to themselves run a severe risk of contacting either the specified viruses, or indeed contacting other viruses if a needle, once used, is reused in an unsterilised form. Various attempts have been made to provide a safe system for disposal of such needles once used but such prior proposals have had deficiencies.

OBJECT OF THE INVENTION

It is an object of this invention to provide .apparatus for housing used surgical needles in a substantially safe manner.

SUMMARY OF THE INVENTION

This invention in one broad form provides a housing for said housing comprising a base adapted to be located on a substantially flat surface, a body adapted for location therein of a needle, a skirt integral with or dependent from the end of the housing body remote from the base thereof and a securement means adapted to retain within the body of said needle housing, a needle once located therein.

It is preferred that the base of the needle housing of this invention be circular and be provided on its underside with a friction surface of toughened rubber for example having anti-slip properties, or alternatively, any anti-slip adhesive means such as a pad impregnated with adhesive material, that pad being covered with a removable plastics or other shield. For example, the removable plastics or other shield may be a hot melt resin rubber base tape. Once the plastics shield is removed from the adhesive material, the housing base may be located on or secured to a flat surface such that when the housing itself is held by the left hand (of a right handed person) the housing will resist movement relative to the base on which it is located, although the housing might be removed by hand pressure from that base after a needle is secured in the housing.

It is further preferred that the aforesaid skirt located at the opposite end of the needle housing from the base, be annular and be integral with the housing.

It is further preferred that the securement means be provided by a rib protruding within the housing in an annular manner and adapted to prevent removal therefrom of a used needle, once that used needle is located In the needle housing of this invention.

It is further preferred that the securement means be adapted to frictionally engage an annular or frusto-conical peripheral surface of a needle boss in which the needle is supported. Such frictional engagement is aimed at retaining the needle boss such that prior to use, the needle boss and needle will be securely retained within the housing.

It is further preferred that an O-ring or any other annular ring be provided, being adapted to locate on the upper surface of the skirt and in contact with the needle boss prior to the needle's use. Such an annular ring prevents accidental full insertion of the needle into the housing prior to its use. Upon first removal of the needle from the housing, the annular ring may be discarded.

It is further preferred that a luminous band or other indicator be provided on the upper surface of the skirt. Such a luminous band may enable a user to guide a needle into the housing in conditions of poor lighting.

BRIEF DESCRIPTION OF THE DRAWINGS

Preferred forms of the present invention will now be described by way of example with reference to the accompanying drawings, wherein:

FIG. 3 depicts a needle housing of a second embodiment with a needle, attached to a syringe, being partly located in that housing prior to use; and FIG. 4 depicts the needle housing according to FIG. 3 with a needle, attached to a syringe, wholly located therein after use.

DESCRIPTION OF THE PREFERRED EMBODIMENTS

Figure 1:
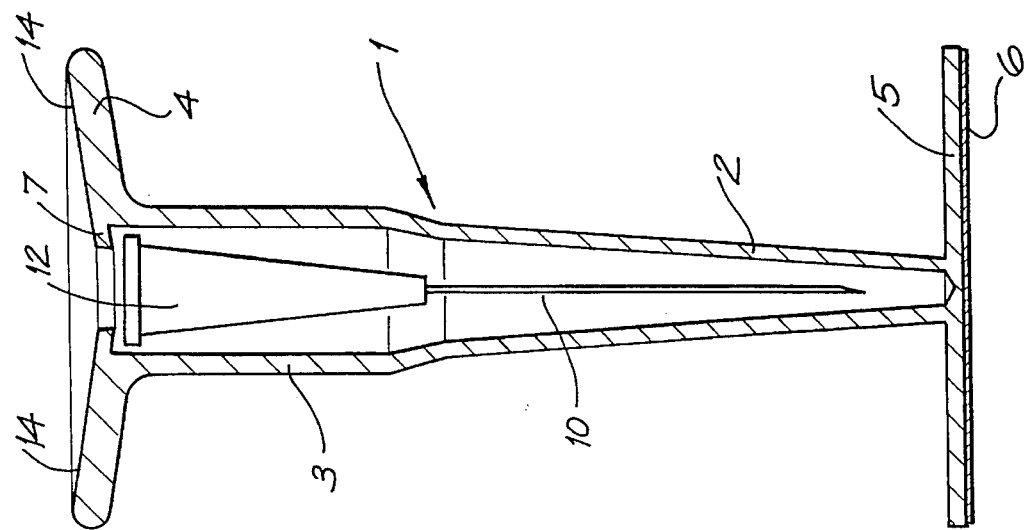
FIG. 1 depicts a needle housing of a first embodiment with a needle being partly located in that housing prior to use.
Figure 2:
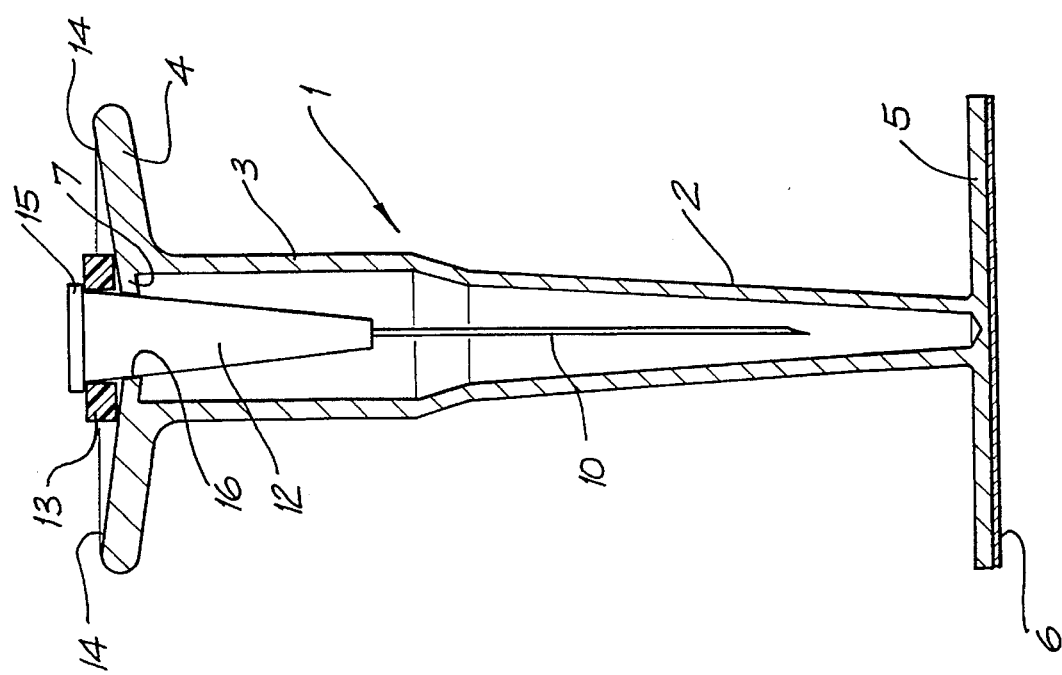
FIG. 2 depicts the needle housing according to FIG. 1 with a needle wholly located therein after use.

In FIGS. 1 and 2 of the accompanying drawings there is schematically depicted a needle housing 1 comprising a conical wall portion 2 and a cylindrical wall portion 3 with annular skirt 4 and annular base 5. Base 5 has located beneath it a layer of adhesive impregnated material 6 or alternatively a roughened anti-slip friction surface such as rubber for example, to allow needle housing 1 to be securely placed upon a flat surface.

An internal annular rib 7 extends inwardly from skirt 4 and is formed integrally therewith. Annular rib 7 is preferably continuous, although alternatively, rib 7 may be replaced by a plurality of stopper (or teeth) members or other securement means. Rib 7 is adapted to frictionally engage the outer surface of needle boss 12 prior to the needle's first use. The relevant area of frictional engagement is indicated at 16 in FIG. 1.

As depicted in FIG. 1 an O-ring 13 is provided above the annular skirt 7 and surrounds needle support 12. O-ring 13 is an individual component to be discarded upon the first removal of needle boss 12 completely from housing 1. O-ring 13 serves the purpose of preventing inadvertent insertion of needle boss 12 into housing 1 prior to use.

In use, housing 1 is attached or otherwise supported above a fixed horizontal surface and is adhered thereto or otherwise secured against slipping thereon by way of adhesive or anti-slip surface 6. Housing parts 2 or 3 may then be held by the thumb and one or more fingers of a user. Annular skirt 14 protects this portion of the operator's anatomy should the needle be detached from the syringe or should the syringe be misdirected in an attempt to locate needle 10 in housing 1. To this end, a luminous band 14 is provided in the upper surface of skirt 4. Once the needle support 10 is introduced into the housing 1, an annular flange 15 provided about the periphery of needle boss 12 passes rib 7 at which point the syringe may be removed from its contact with needle 10 and needle boss 12. As the peripheral diameter of boss 12 is greater than or equal to the internal diameter of rib 7 in its relaxed state, a tight frictional engagement aids to prevent unwanted removal of needle 10 and needle boss 12 from housing 1. At this stage, housing 1 may be removed from the surface beneath face 5. The needle housing 1 with its contents of used needle 10 removed from syringe 11 may now be disposed of appropriately.

In accordance with a second embodiment of the invention depicted in FIGS. 3 and 4, housing 1 comprises a cylindrical wall portion 2 and conical wall portion 3 with annular skirt 4 and annular base 5. Base 5 has located beneath it the layer of adhesive impregnated material 6 or other non-slip material to allow needle housing 1 to be secured or prevented to slip upon a flat surface.

Internal annular rib 7 is integral with the inner wall 3A of housing 1 and is preferably continuous although, in a less preferred embodiment of this invention, continuous rib 7 may be replaced by a plurality of stop members integral with wall 3A.

As is the case with the first embodiment described above, annular rib 7 is adapted to frictionally engage at 16 the outer peripheral surface of needle boss 12 prior to use.

When a needle attached to a syringe is used, housing 1 is attached to a fixed surface and is held by the thumb and one or more fingers of the left hand of a right handed person. Annular skirt 4 protects this portion of the operator's anatomy should the needle be detached from the syringe or should the syringe be misdirected in an attempt to locate needle 10 in housing 1. When needle 10 is introduced to housing 1 by an operator holding syringe 11, needle boss 12 is forced into housing 1 until rim 12A (see FIG. 3) thereof is located within housing 1 beneath rib 7 thereof. Syringe 11 may then be removed from its contact with needle 10 and needle boss 12, rib 7 retaining needle 10 and needle boss 12 wholly within needle housing 1. Thus needle 10 becomes isolated within needle housing 1 and needle housing 1 may be removed from its contact with the flat surface upon which it is located and needle housing 1 with its contents of used needle 10 removed from the syringe disposed of appropriately.

It will be seen that the invention the subject of this application provides a safe system for the disposal of used needles and substantially ensures single use only of any given needle.

We claim:

1. A housing for releasably securing a needle therein so as to enable the needle to be separated from the housing and used with a syringe and after said use to receive the needle for disposal with the housing, said housing comprising a base adapted to be placed on a substantially flat surface, a hollow body for receiving therein, a needle boss and a needle supported by said needle boss, said body having opposite ends at one of which said base is disposed, a skirt located at the other of the ends of the hollow body remote from said base, said skirt being shaped to protect a person holding the body from contact by a needle misdirected towards location in said housing, said base and said skirt being of substantially similar width, said skirt defining an opening for said hollow body at said one end through which said needle boss and said needle can be inserted into said hollow body, said skirt having an internal peripheral surface at said opening, a securement means comprising at least one stopper member located on said internal peripheral surface of said skirt and projecting inwardly therefrom to permanently retain within the hollow body of the housing, said needle boss and said needle when located therein after use with a syringe, and an annular ring located above and in contact with said skirt to surround said needle boss adjacent said skirt prior to use of said needle.

2. A housing for releasably securing a needle as defined in claim 1, wherein said skirt is substantially annular and said base is circular, said base having a diameter substantially equal to an outside diameter of said skirt.

3. The housing of claim 1, further comprising an anti-slip surface on the underside of the base.

4. The housing of claim 1, further comprising an adhesive surface on the underside of the base.

5. The housing of claim 4, wherein the adhesive surface comprises a pad impregnated with adhesive material.

6. The housing of claim 5, wherein the pad is covered with a removable shield.

7. The housing of claim 1, wherein said at least one stopper member comprises an annular rib protruding within the housing.

8. The housing of claim 1, further comprising a luminous band or indicator on an upper surface of the skirt.

9. The housing of claim 1, wherein the securement means frictionally retains the needle boss.

10. The housing of claim 1, wherein a maximum peripheral diameter of the needle boss is greater than or equal to the relaxed state internal diameter of the securement means.

11. The housing of claim 1, wherein the securement means is integral with the housing.

* * * * *